United States Patent [19]
Heil

[11] Patent Number: 5,968,082
[45] Date of Patent: Oct. 19, 1999

[54] PACEMAKER LEAD LOCKING MECHANISM

[75] Inventor: Horst Franz Heil, Bad Steben, Germany

[73] Assignee: Biotronik Mess- und Therapiegeraete Gmbh & Co. Ingenieurbuero Berlin, Berlin, Germany

[21] Appl. No.: 08/808,994

[22] Filed: Mar. 3, 1997

[30] Foreign Application Priority Data

Mar. 4, 1996 [DE] Germany ............... 196 09 367

[51] Int. Cl.⁶ ............... A61N 1/375; A61N 1/05
[52] U.S. Cl. ............... 607/37; 607/38
[58] Field of Search ............... 607/37, 38

[56] References Cited

U.S. PATENT DOCUMENTS

| | | | |
|---|---|---|---|
| 4,583,543 | 4/1986 | Peers-Trevarton | 607/1 |
| 5,070,605 | 12/1991 | Daglow et al. | 607/37 |
| 5,261,395 | 11/1993 | Oleen et al. | |
| 5,730,628 | 3/1998 | Hawkins | 607/37 |
| 5,807,144 | 9/1998 | Sivard | |

FOREIGN PATENT DOCUMENTS

| | | |
|---|---|---|
| 0339877 | 11/1989 | European Pat. Off. ....... A61N 1/375 |
| 0590756 | 4/1994 | European Pat. Off. ....... A61N 1/375 |
| 3311510 | 12/1983 | Germany . |
| 95/10324 | 4/1995 | WIPO . |

*Primary Examiner*—William E. Kamm
*Assistant Examiner*—Carl H. Layno
*Attorney, Agent, or Firm*—Venable; George H. Spencer; Catherine M. Voorhees

[57] ABSTRACT

An implantable electrostimulation device and an electrode lead is devised where for the electrical connection of the electrode lead, the top portion of the electrostimulation device has a securely installed connecting socket with radially inward pointing contact and holding devices on its inside wall, which are designed to engage with the electrode lead contact. The contact and holding means are formed by a plurality of cam and projection regions that are securely connected to the inside wall or formed out of this wall and are each at a predetermined angular distance in a circumferential direction of the socket. The electrode lead has a pin or annular contact for inserting into a connecting socket of the electro-stimulation device, which has radially outward pointing contact and holding units on its surface for engaging with the connecting socket. These units are formed by a plurality of cam or projection regions that are securely connected to the surface of the pin or annular contact or are formed from it and are located at a fixed, predetermined angular distance in circumferential direction of the pin or annular contact.

14 Claims, 9 Drawing Sheets

PACEMAKER LEAD LOCKING MECHANISM

BACKGROUND OF THE INVENTION

1. Field of The Invention

The invention concerns an implantable electrostimulation device, for example a pacemaker or defibrillator, with a top portion for the electrical connection of an electrode lead with a fixedly installed connecting socket and the inside wall of the fixedly installed connecting socket having radially inward pointing contact and holding means for engaging an electrode lead contact.

The invention further is directed to an electrode lead for an implantable electrostimulation device with a pin or annular contact for inserting into a connecting socket of the electrostimulation device.

2. Description of the Related Art.

From DE-A-3 311 510, an arrangement is known for connecting the proximal end of a bipolar electrode lead to a pacemaker, wherein the electrode lead has a front pin contact and an annular contact being disposed in distal direction behind it. For the connection to the pacemaker, the proximal pin contacts for the electrode lead are inserted into a hollow cylindrical, so-called end block where they are secured in place with a screw. The locking screw in the end block is designed to ensure a sufficient electrical contact on the one hand, and on the other hand is designed to provide protection against an undesired axial displacement of the lead contact within the end block, so that the proximal end of the bipolar electrode lead cannot detach itself from the pacemaker. The second connection for the electrode lead, which is provided in distal direction behind the pin contact and is designed as annular contact, is inserted into a sleeve with three notches on its inside surface in order to make contact. A wire that is essentially bent into a circle is inserted under mechanical prestressing into these notches in such a way that the annular contact is electrically connected at three points with the wire, provided the pin contact for the electrode lead is in the end block designed for it.

This solution has the disadvantage that the screw-connection and the use of a wire that is essentially bent into a circle and inserted into a sleeve does not ensure a large-surface contacting and in addition only provides insufficient security against an unintended disconnecting of the connection during an axial stressing of the electrode lead.

In U.S. Pat. No. 4, 583, 543, an arrangement for connecting a bipolar electrode lead to a pacemaker is suggested where in order to connect an electrode lead that is thinner than the originally planned one, an adapter is provided in the top portion of the pacemaker. The connection between the adapter and the electrode lead is a frictional connection that is created as a result of a multiple contact that essentially occurs only at contact points along a single circumferential line of contact for the electrode lead. The safety against a loosening of the connection during an axial stressing of the electrode lead appears to be insufficient.

EP-A-0 339 877 furthermore discloses a connector system for pacemakers, which provides in the top portion of the pacemaker two metal cylinders with inside-positioned spring wires for contacting the electrode lead connections. The safety against a disconnecting of the electrical connection between electrode lead and pacemaker during a mechanical stressing in axial direction is insufficient in this case as well, since this is countered only by a frictional connection in essentially linear contact regions.

SUMMARY OF THE INVENTION

Starting with the shortcomings in the prior art, it is the object of the invention to create an electrostimulation device of the aforementioned type and an electrode lead that can be connected to the electrostimulation device, which can both be connected easily and quickly and which, when connected, also offers a high security against the axial pull on the electrode lead.

The solution to problems associated with the prior art is achieved in an implantable electrostimulation device where the contact and holding means are formed by a plurality of cam and projection regions that are tightly connected to the inside wall of the connecting socket or shaped from the inside wall so that the plurality of cam and projection regions are respectively at a fixedly predetermined angular distance in a circumferential direction of the socket.

Likewise, the problems are solved by an electrode lead which includes radially outward pointing contact and holding means located on the surface of the electrode lead's pin or annular contact where the contact and holding means are formed by a plurality of cam or projection regions that are securely connected to the surface or are formed from the surface and are positioned at a fixed, predetermined angular distance in a circumferential direction of the pin or annular contact.

The invention includes the idea of providing a plurality of contact regions for a relatively large-surface electrical contacting and for producing a positive or at least a highly effective frictional connection that is rigidly installed at the connecting socket for the electrostimulation device and/or at least at one of the contacts of the electrode lead connector, which results in a high resistance to an essentially axially directed pulling force.

These contact and holding means in the form of cam or projection regions are preferably arranged in groups in several planes that are parallel to each other and in axial rows.

In order to form the radially inward pointing contact and holding means for the connecting socket in the top portion of the pacemaker, one technologically advantageous variant of the invention provides that a sleeve with bridge-type, elastic projecting regions be inserted into the socket, which are produced especially through stamping and bending from a sheet type material having springy qualities and preferably a high conductivity. This sleeve encloses tightly and elastically a conventional pin or annular contact for an electrode lead and provides a good electrical contact as well as a high resistance against axial pulling forces as a result of the relatively large effective contact surface and suitable contact pressure.

For another preferred embodiment, recesses are respectively provided between several projections of the connecting socket that are grouped in circumferential direction, into which projections of a ring contact (or the pin contact or both) of the electrode lead engage when the electrode lead is plugged in and which correspond in form and arrangement with the recesses. A subsequent turning of the inserted electrode lead causes the projections of the electrode lead contacts to grip behind those of the connecting socket. If several contact and holding means are provided, especially in axial rows, then these engage alternately in the recesses between them. The interlocking of the projections creates an enlarged electrical contact surface and a form-fitting connection between the two, which safely prevents the pulling out of the electrode lead from the connecting socket. The electrical and mechanical qualities are further improved if the cam or projection regions are arranged as such and their engagement surfaces are designed such that they make operative contact by creating a surface pressure. This surface pressure on the one hand advantageously prevents an undesired turning movement of the electrode lead to an angle position where the axial lock would be eliminated, and results advantageously in a high contact pressure.

For a simple, but effective design, three or flour contact and holding means with identical designs each are distributed evenly over the circumference of the connecting socket or the annular contact—meaning they are arranged at an angular distance between center planes of 120° or 90°.

In a special configuration, the side surfaces that form the flanks of the cam-shaped contact and holding means are arranged such that they are inclined slightly toward each other in circumferential direction, so that the cams have a slightly wedge-shaped cross sectional profile. In a simple way, this results in a high surface pressure and additionally achieves that the screwing-in of the electrode lead can take place easily, even from an inserted position where the angle position of the connector relative to the socket is not optimal. Furthermore, the wedge-shaped cross sectional profiles of the contact and holding means provide a safety against an unintended overturning of the electrode lead into an angle position where the contact and holding means would not be operatively engaged or would make only insufficient contact.

In accordance with one favorable modification, the center plane for the cams or projections of the electrode lead is swiveled by an angle of a few degrees relative to the longitudinal axis of the plug (similar to the blades of a ventilator wheel). The corresponding cams or projections of the connector socket are chamfered on both sides, as seen in circumferential direction. This too permits the screwing-in of the electrode lead in a favorable way, even if the projections and recesses are not exactly aligned following the insertion.

In accordance with one variant of the invention, spring elements extending in circumferential direction are provided on the wall of the connector socket, which have separate fastening points on the sleeve. The spring elements are subjected to an elastic elongation if the pin or annular contact of the electrode lead is inserted into the connector socket. This in turn results in the surface pressure with the electrode lead contact which is desirable to achieve a high degree of safety against pulling out.

Such a design for the connector socket does not provide for a profiling of the annular contact surface at the proximal end of the electrode lead through additional contacting means. The annular contact diameter is simply selected larger than the clear diameter for the connector socket (between the non-elongated spring elements).

BRIEF DESCRIPTION OF THE DRAWINGS

Advantageous modifications of the invention are described in more detail in the following with the aid of the figures in which.

DESCRIPTION OF THE PREFERRED EMBODIMENTS

Figure 1:
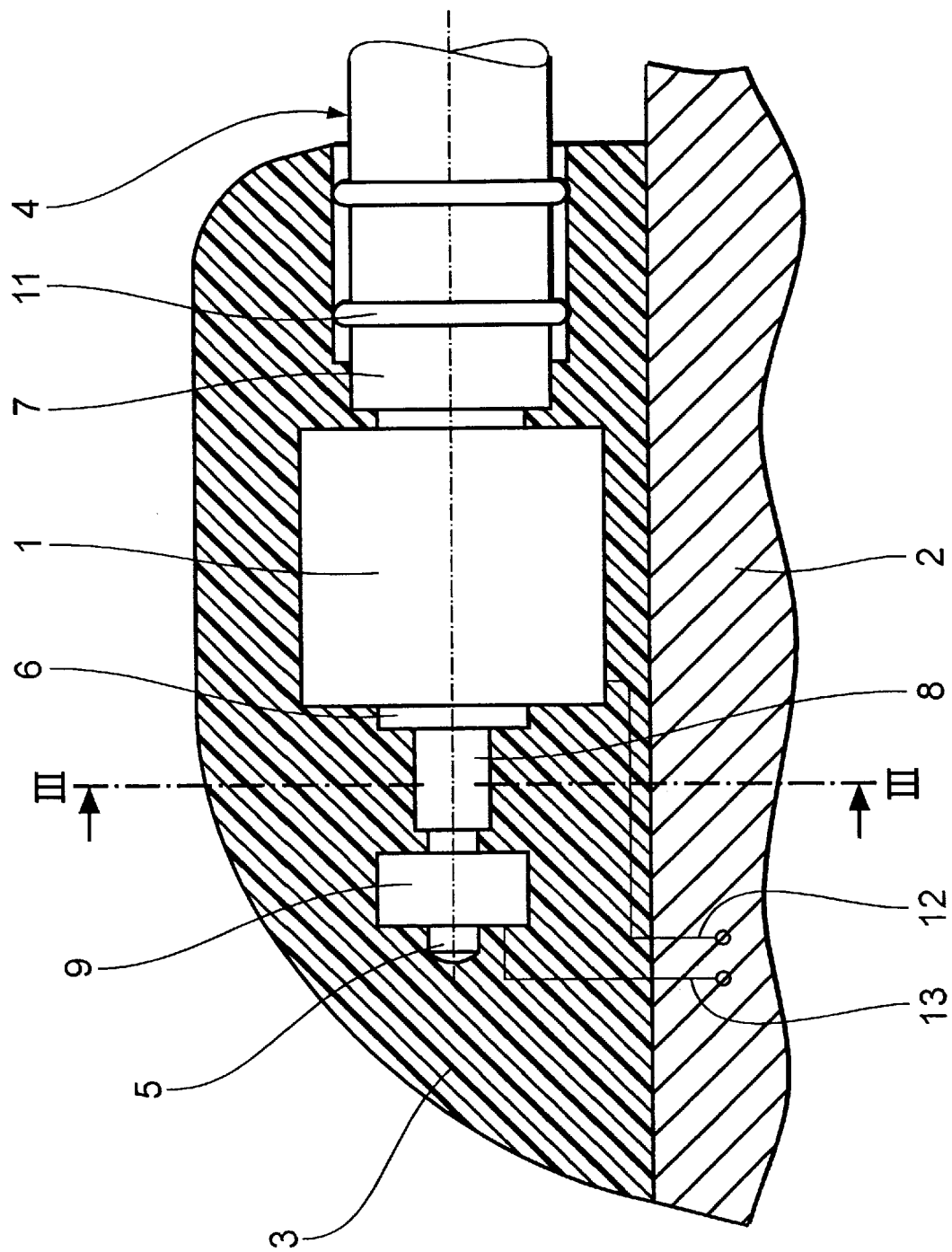
FIG. 1 is a diagrammatic, partial view of the top portion of a pacemaker with a connected electrode lead.

FIG. 1 is a sketch of the top portion 3 of a pacemaker 2 with connected bipolar electrode lead 4. The contacts 5 and 6 that are located at the proximal end of the electrode lead are separated from one another by an insulation 8. An annular contact 6 for the electrode lead 4 is provided coaxial to the pin contact 5. Connecting sockets 1, 9 are provided in the top portion 3 of the pacemaker and are respectively assigned to one of the contacts 5, 6 of the electrode lead 4. The electrical connection between the connector sockets 1, 9 and the (not shown) electronic components of the pacemaker 2 is made via internal leads 12, 13. Two sealing rings 11 are provided at the outside insulation 7 for the electrode lead 4, which prevent body fluid from entering via the insertion opening in the top portion once the pacemaker is implanted.

Figure 2:
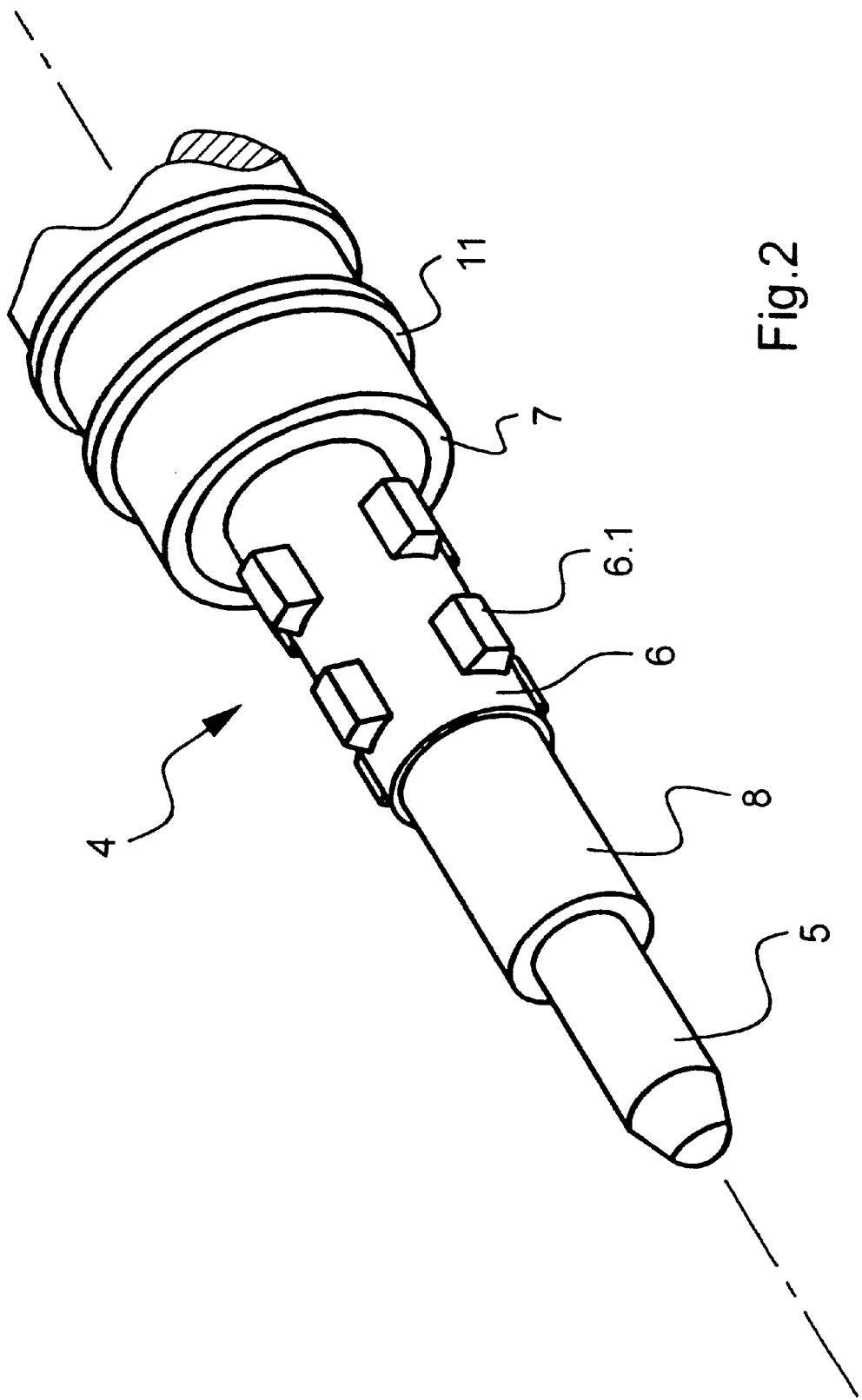
FIG. 2 is a perspective, partial view of a preferred embodiment of the invention.

FIG. 2 shows the proximal end of the electrode lead 4 in a perspective section. While the pin contact 5 has a smooth surface, a plurality of connector cams 6.1, which extend radially outward and are shaped like truncated pyramids, are provided on the surface of the annular contact 6 for lead 4 that is separated from the pin contact 5 by an insulation 8. The connector cams 6.1 that are distributed evenly across a circumferential line of the annular contact form a cam group, which represents a first segmenting of the annular contact in circumferential direction. Several cam groups are provided for a second segmenting of the annular contact 6, which while spaced apart equally are arranged in rows that are spaced apart equally in axial direction of the electrode lead 4.

The outer insulation 7 of the electrode lead 4 carries two sealing rings 11, which tightly seal the insertion opening in the top portion of the pacemaker against moisture.

Figure 3:
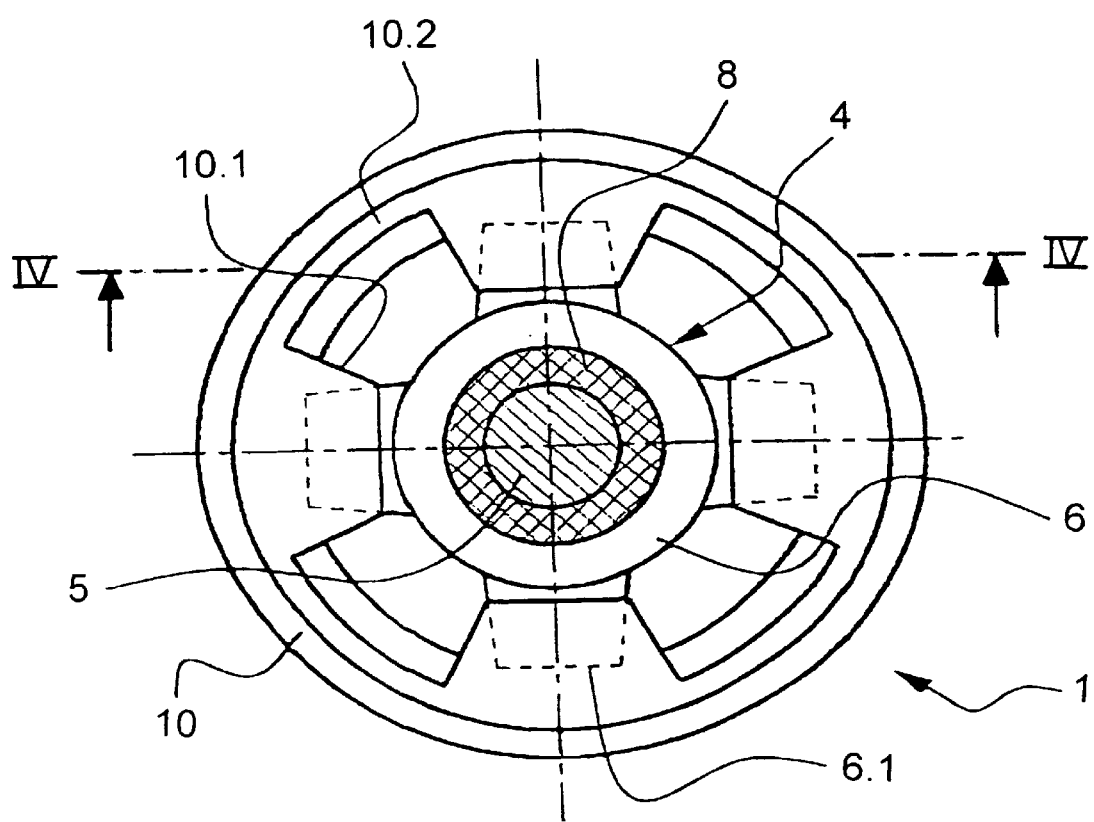
FIG. 3 is a representation of a, partial view along the line III . . . III according to FIG. 1.

FIG. 3 shows a connection arrangement, comprising the connecting socket 1 in the top portion of the pacemaker and the electrode lead 4, in the form of a section along the line III. . . III according to FIG. 1, wherein the electrode lead 4 has been turned clockwise by 90° around its longitudinal axis following the axial insertion into the socket. The connecting socket 1 is composed of an outside sleeve 10, into which an inside sleeve 10.2 is inserted. The inside sleeve 10.2 has on its inside surface a plurality of radially inward pointing socket cams 10.1, between which uniformly large recesses are provided through tangential segmenting. Grouping the socket cams 10.1 at a certain distance to each other in axial direction results in recesses (see FIGS. 4 and 5). Their extension in circumferential direction is adjusted to the dimensions of the socket cams 6.1 along the periphery of the annular contact 6 in such a way that the socket cams 6.1 can be moved axially in the recesses when the electrode lead 4 is inserted into the connecting socket 1. During the turning of the electrode lead 4 following the insertion into the connecting socket, the connector cams 6.1 are swiveled into the recesses existing in axial direction between the socket cams 10.1 of the connecting socket 1.

As a result of this, a bayonet-type connection is created in a favorable way between the socket and connector cams during the screwing-in of the electrode lead, which ensures a sufficient surface contact with simultaneously increased surface pressure at the edge regions (compare the position 13 according to FIG. 5) of the cam flanks. This safeguards the connection arrangement against a detaching of the electrode lead 4 in case of mechanical stresses in axial direction.

Figure 4:
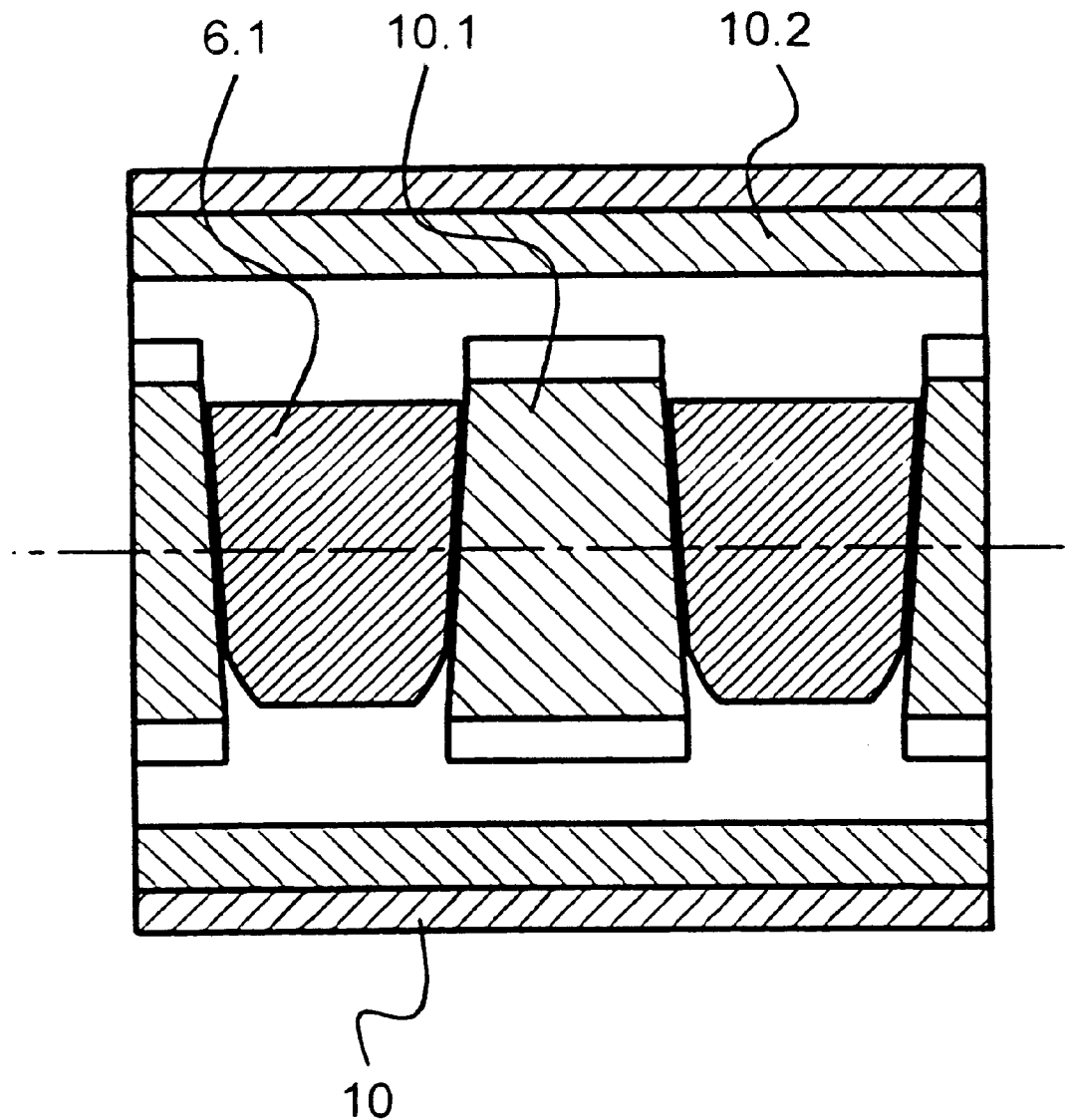
FIG. 4 is a cross-section view taken along the line IV . . . IV as shown in to FIG. 3.
Figure 5:
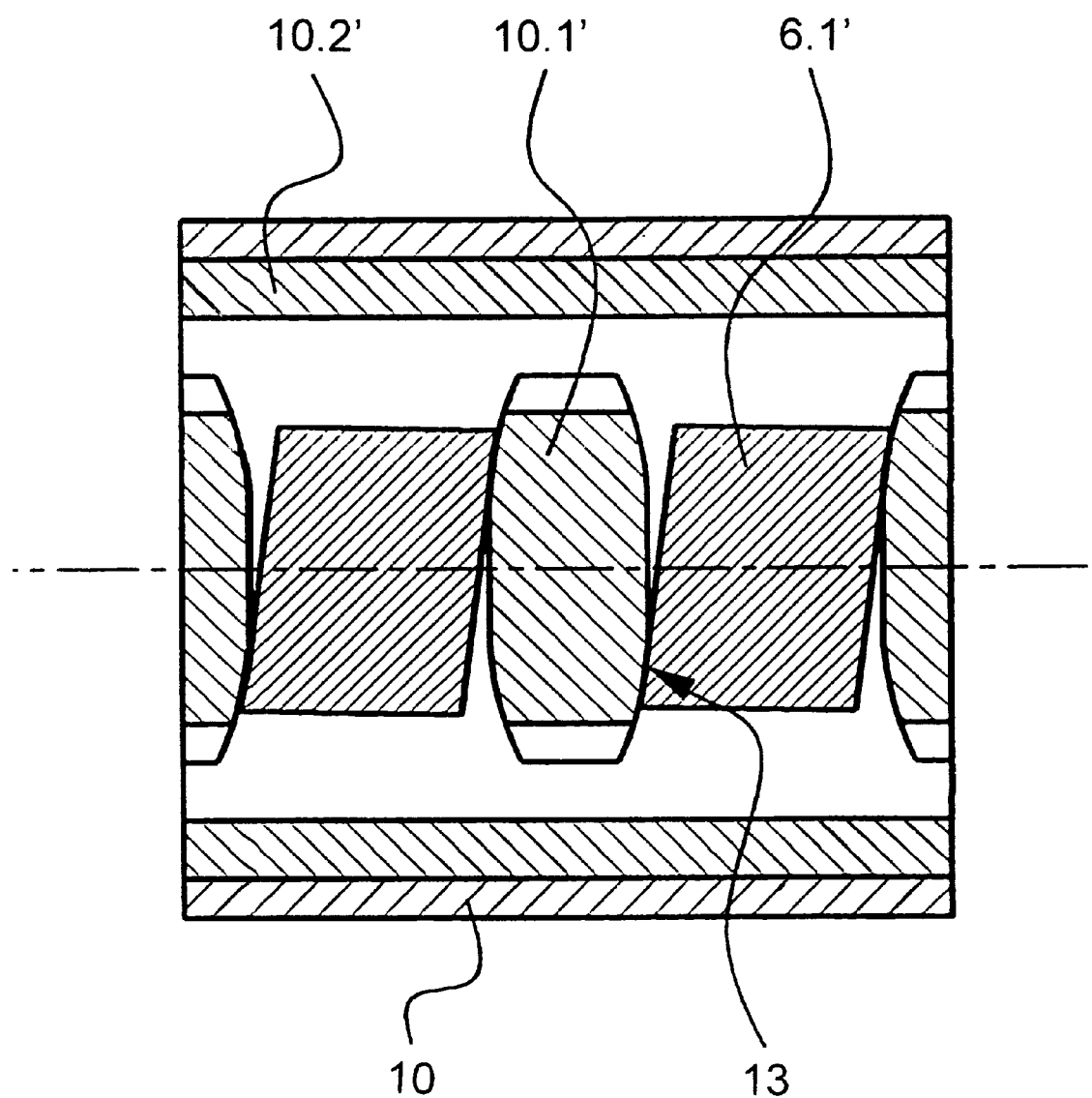
FIG. 5 is a sectional view of a modification of the invention relative to FIG. 4.

Advantageous embodiments of the connector and socket cams are illustrated in the FIGS. 4 and 5 as view of a section along the line IV . . . IV, according to FIG. 3. The flanks (side surfaces) of the individual cams 6.1, 6.1', 10.1, 10.1' are basically arranged or designed such that on the one hand, during the turning of the electrical lead this permits an easy insertion of the connector cams 6.1, 6.1' of the annular contact into the recesses present at the inside of inside sleeve 10.2, 10.2' of the connecting socket in axial direction between the socket cams 10.1, 10.1'. On the other hand, this turning movement is limited with simultaneous locking of the socket cams 6.1, 6.1' and thus offers protection against an overturning, which would no longer ensure the contacting. The maximum turning angle has a value of 90°.

In accordance with FIG. 4, the flanks of the connector cams 6.1 as well as the flanks of the socket cams 10.1 are inclined toward each other in tangential direction, so that an essentially wedge-shaped cross sectional profile results. The individual wedges have a uniformly large opening angle as seen in tangential direction. After the turning of the electrode lead is completed, this results advantageously in a frictional and form-locking connection between the contact means for a large-surface contacting and sufficient surface pressure at the cam flanks.

The sectional view according to FIG. 5 shows connector cams 6.1 of the annular contact for the electrode lead, which have a cross sectional profile in the shape of a parallelogram and are simultaneously swiveled by a slight measure around their radially extending longitudinal axis. The flanks of the socket cams 10.1' of socket portions 10, 10.2' of the connecting socket in the top portion of the pacemaker (compare the positions 1, 2 and 3 according to FIG. 1) have a chamfering on both sides in tangential direction, which makes it easier for the connector cams 6.1' to engage into the recesses between the socket cams 10.1' in axial direction if the connector cams 6.1' are not exactly aligned with the respective recesses.

Figure 6:
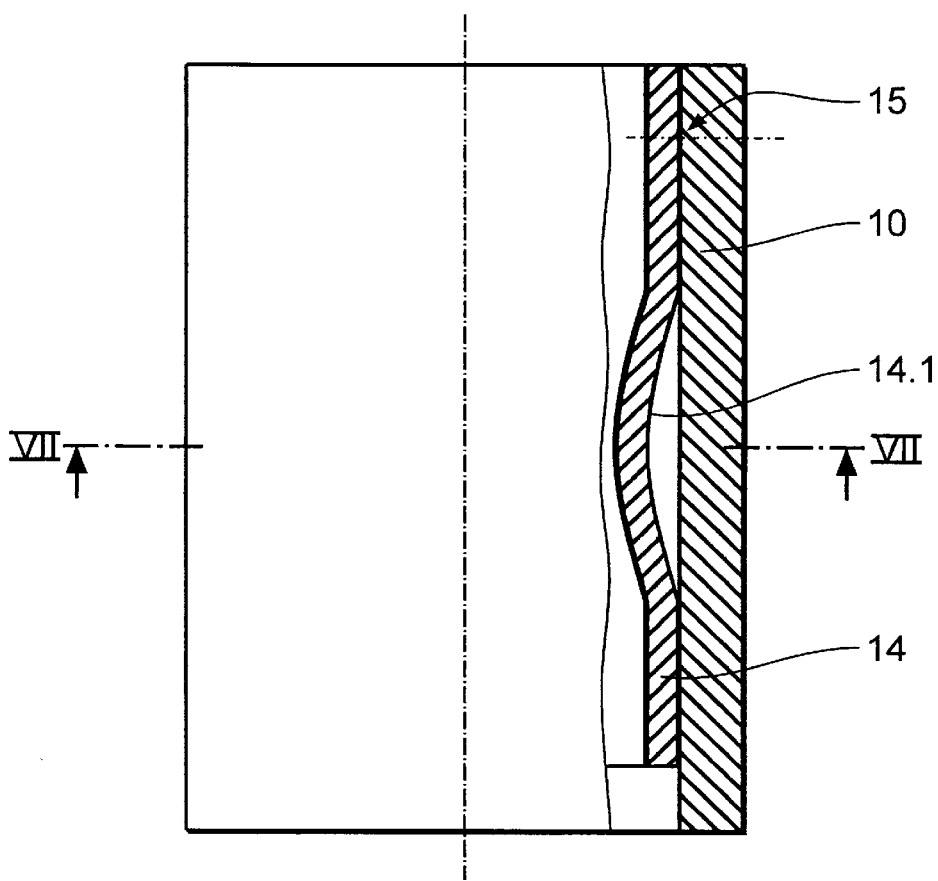
FIG. 6 is a partial longitudinal section through a connection socket of another embodiment of the invention.
Figure 7:
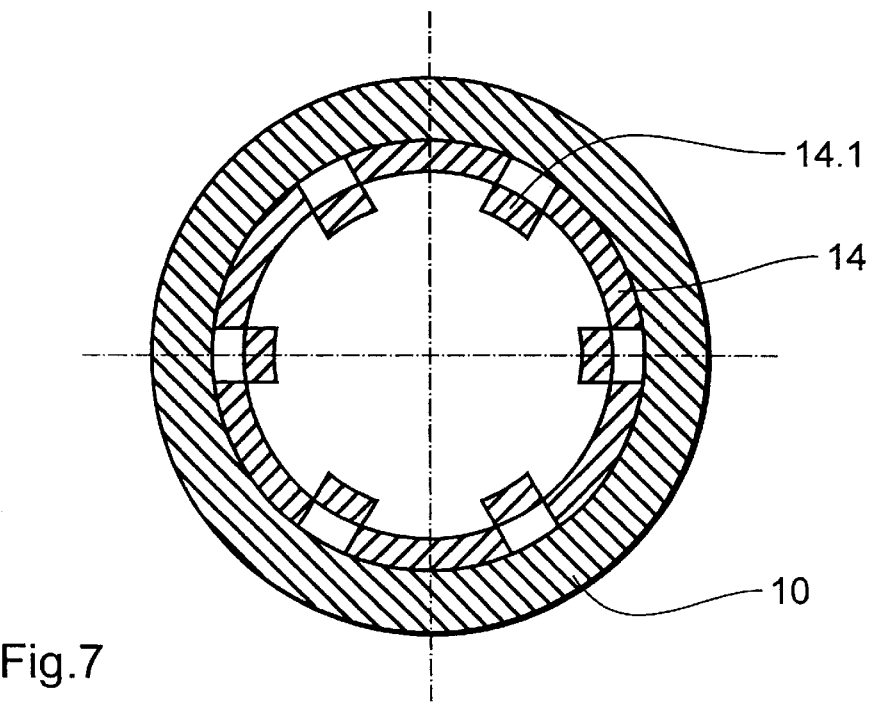
FIG. 7 The representation of a section through the line VII . . . VII as shown in FIG. 6.

The representations corresponding to the FIGS. 6 and 7 show a partial longitudinal section through a connecting socket 1 or 9 or a cross sectional view of this socket (section along the line VII . . . VII according to FIG. 6). In a closed outside sleeve 10, the connecting socket has an inside sleeve 14 with strip-type contact spring segments 14.1, which extend radially inward as well as have an axial extension.

Figure 8:
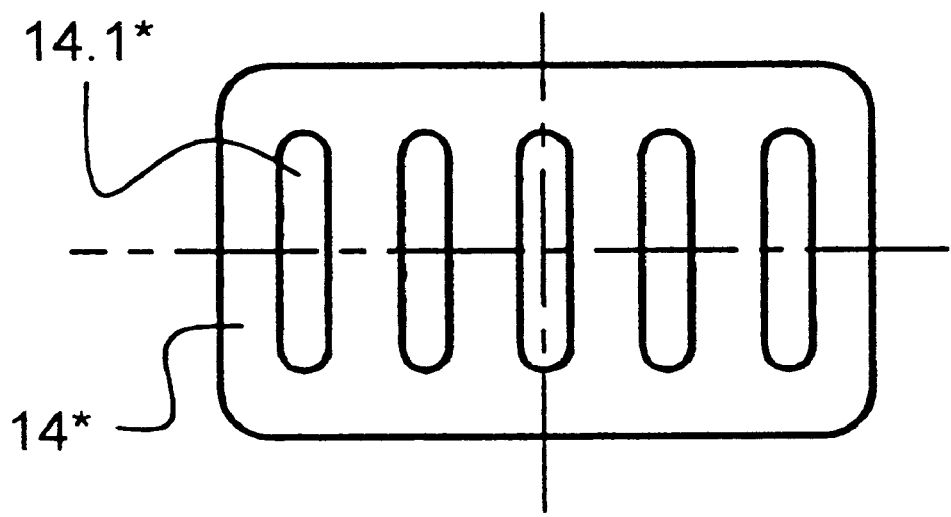
FIGS. 8 and 9 show two different production stages for the sleeve shown in the FIGS. 6 and 7.
Figure 9:
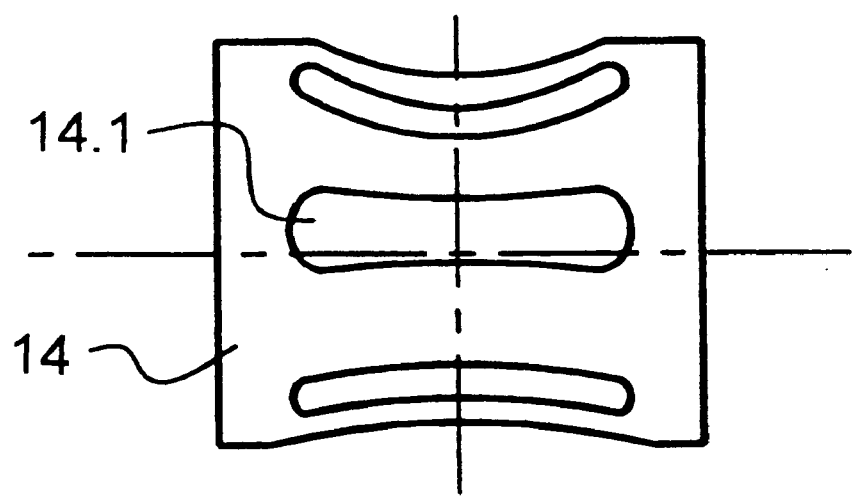

FIGS. 8 and 9 show the inside sleeve 14 in two processing stages. The sleeve 14 is manufactured from a resilient, sheet-type material 14* and is shaped into the required cylindrical form through stamping or forming, wherein the surface regions 14.1* are simultaneously stamped to form the contact means 14.1.

At one of its ends, the inside sleeve 14 is Connected to the inside edge of the outside sleeve 10 by laser welding it on with several welding points 15. This one-sided fastening ensures in a simple way that the sleeve can elongate in axial direction if the smooth pin contact or an annular contact with smooth design (deviating from the above described embodiments) of the proximal end of the electrode lead is inserted into the connecting socket. As a result of this, the resilient effect of the contact spring segments 14.1 of sleeve 14 that is necessary for the contacting is constantly maintained.

Figure 10:
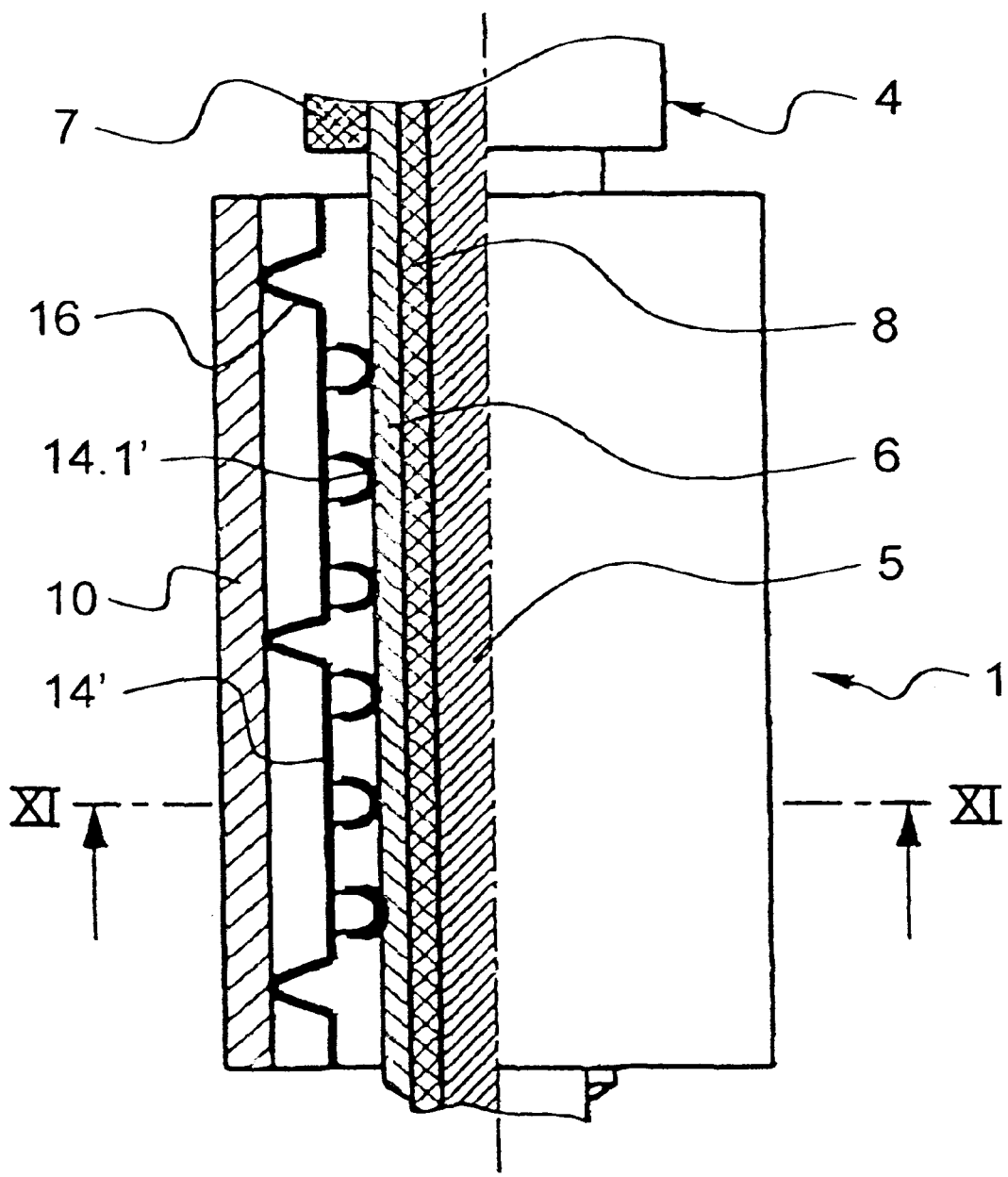
FIG. 10 is a partial longitudinal section through yet another embodiment of the invention and FIG. 11 is a cross-section view taken along the line XI . . . XI of FIG. 10.
Figure 11:
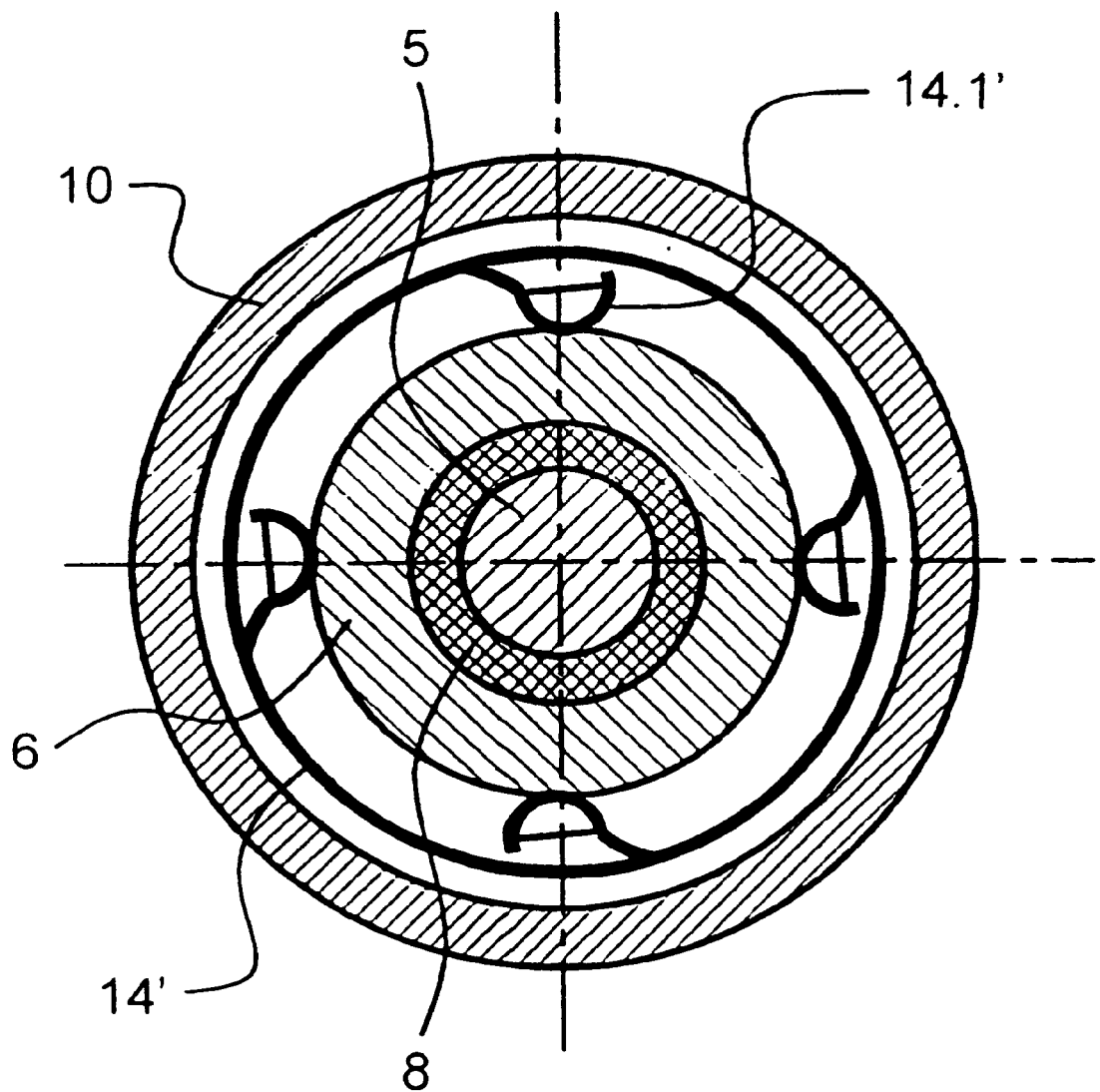

The FIGS. 10 and 11 show as further embodiment a connection socket 1 in a partial longitudinal section or cross sectional illustration along the line XI . . . XI according to FIG. 10. The proximal end of the electrode lead 4 is inserted into the connecting socket 1. The inside sleeve 14' that is positioned in the outside sleeve 10 and is fashioned from spring steel sheet has several radially outward pointing annular rings 16, which ensure a tight seat for the inside sleeve 14'. The four contact springs 14.1', which are distributed evenly along the sleeve circumference in the sectional plane, have a strip-type design and are fastened with one side to the sleeve wall. They point toward the socket inside space, wherein their free end has an essentially hemispherical shape and wherein they support themselves resiliently on the annular contact 6. The hemispherical form makes it easier to insert the cylindrical annular contact 6 for the electrode lead 4. The arrangement in rows of the above-described contact springs in axial direction of the connecting socket 1 permits a safe contacting of the annular contact through the respective number of electrical contact surfaces and frictional connection regions and ensures a tight seat of the proximal end of the electrode lead in the top portion of the pacemaker. The invention is not limited in its design to the above-mentioned preferred exemplary embodiments. Rather, a plurality of variations are conceivable, which make use of the illustrated solution, even for a differing design.

I claim:

1. An implantable electrostimulation device with a top portion for the electrical connection of an electrode lead with a fixedly installed connecting socket, the inside wall of which has radially inward pointing contact and holding means for engaging with an electrode lead contact wherein the contact and holding means are formed by a plurality of cam and projection regions that are tightly connected to the inside wall or shaped from it and which are respectively at at least one of a fixedly predetermined angular distance in a circumferential direction of the socket and an axial distance of the socket, the contact and holding means being in a form-locking and a frictional engagement with respectively arranged and formed regions that are formed as part of a pin or annular contact of an electrode lead.

2. The electrostimulation device according to claim 1, wherein the contact and holding means are elastic and have one of a radially deformable projection, an axially deformable projection or a radially and axially deformable projection extending in the direction of the socket for an essentially frictional connection with a pin or annular contact of an electrode lead.

3. The electrostimulation device according to claim 1, wherein at least two cam or projection regions are arranged in rows in an axial direction while the position in a circumferential direction coincides.

4. The electrostimulation device according to claim 1, wherein the cam or projection regions have essentially radially extending, front and back side surfaces, which are inclined toward each other.

5. The electrostimulation device according to claim 1, wherein at least three cam or projection regions are arranged in separate planes that extend crosswise to the longitudinal axis for the connecting socket, and have the same angular distance to each other.

6. The electrostimulation device according to claim 1, wherein the connecting socket has an inside sleeve that is completely fashioned from a conductive spring steel sheet, which sleeve has symmetrically arranged spring bridges as the cam or projection regions.

7. The electrostimulation device according to claim 1, wherein the contact and holding means are essentially in the shape of runners.

8. The electrostimulation device according to claim 1, wherein the contact and holding means are essentially in the form of a truncated pyramid.

9. An electrode lead for an implantable electrostimulation device with a pin or annular contact for inserting into a connecting socket of the electrostimulation device, said electrode lead comprising radially outward pointing contact and holding means which are formed by a plurality of cam or projection regions that are securely connected to the surface of the pin or annular contact or are formed from the surface and are each positioned at at least one of a fixed, predetermined angular distance in a circumferential direction of the pin or annular contact and axial distance of the pin or annular contact, the contact and holding means being in a form-locking and frictional engagement with corresponding arranged and formed regions of the connecting socket of the electrostimulation device.

10. The electrode lead according to claim 9, wherein at least two cam or projection regions are arranged in rows in an axial direction, while their position coincides in a circumferential direction.

11. The electrode lead according to claim 9, wherein the cam or projection regions have approximately radially extending side surfaces, which are inclined toward each other.

12. The electrode lead according to claim 9, wherein their proximal end is designed in such a way that it is connected inside the connecting socket of the electrostimulation device via one of a form-locking, frictional, or form-locking and frictional engagement between their contact and holding means with those in the socket in particular through surface pressure against their respective neighboring side surfaces, which is the result of a predetermined axial displacement and by turning the end by a predetermined angle.

13. The electrode lead according to claim 9, wherein the contact and holding means are essentially in the shape of runners.

14. The electrode lead according to claim 9, wherein the contact and holding means are essentially in the form of a truncated pyramid.

* * * * *